US009750486B2

(12) United States Patent
Burg et al.

(10) Patent No.: US 9,750,486 B2
(45) Date of Patent: Sep. 5, 2017

(54) TRACKABLE BIOPSY NEEDLE (75) Inventors: Bruce M. Burg, Louisville, CO (US); Steven L. Hartmann, Superior, CO (US)

(73) Assignee: Medtronic Navigation, Inc., Louisville, CO (US)

( * ) Notice: Subject to any disclaimer, the term of this patent is extended or adjusted under 35 U.S.C. 154(b) by 706 days.

(21) Appl. No.: 13/281,001

(22) Filed: Oct. 25, 2011

(65) Prior Publication Data
US 2013/0102878 A1  Apr. 25, 2013

(51) Int. Cl.
A61B 5/00 (2006.01)
A61B 10/02 (2006.01)
A61B 5/06 (2006.01)
A61B 34/20 (2016.01)

(52) U.S. Cl.
CPC .......... *A61B 10/0275* (2013.01); *A61B 5/062* (2013.01); *A61B 34/20* (2016.02); *A61B 2034/2051* (2016.02)

(58) Field of Classification Search
CPC .......... A61B 5/062; A61B 5/063; A61B 5/065
USPC .............................. 600/411, 424; 324/207.11
See application file for complete search history.

(56) References Cited

U.S. PATENT DOCUMENTS

| | | | |
|---|---|---|---|
| 4,188,979 A | 2/1980 | Nakamura et al. | |
| 4,788,987 A | 12/1988 | Nickel | |
| 4,806,182 A | 2/1989 | Rydell et al. | |
| 5,005,592 A | 4/1991 | Cartmell | |
| 5,226,423 A | 7/1993 | Tenerz et al. | |
| 5,538,511 A | 7/1996 | Van Antwerp | |
| 5,591,141 A | 1/1997 | Nettekoven | |
| 5,592,939 A | 1/1997 | Martinelli | |
| 5,762,637 A | 6/1998 | Berg et al. | |
| 5,840,024 A * | 11/1998 | Taniguchi et al. | 600/424 |
| 5,913,820 A | 6/1999 | Bladen et al. | |
| 5,938,602 A | 8/1999 | Lloyd | |
| 5,963,120 A | 10/1999 | Zaviska | |
| 5,983,126 A | 11/1999 | Wittkampf | |
| 6,106,486 A | 8/2000 | Tenerz et al. | |
| 6,201,387 B1 | 3/2001 | Govari | |

(Continued)

FOREIGN PATENT DOCUMENTS

| | | |
|---|---|---|
| AU | 2011245296 A1 | 12/2012 |
| CA | 2797359 A1 | 11/2011 |

(Continued)

OTHER PUBLICATIONS

"InstaTrak 3500 Plus. Applications: ENT. Cranial." http://www.gehealthcare/usen/xr/surgery/products/nav.html (printed Dec. 14, 2009).

(Continued)

*Primary Examiner* — Rajeev Siripurapu
(74) *Attorney, Agent, or Firm* — Harness Dickey (57) ABSTRACT

A trackable biopsy needle assembly including an inner tube of an outer cannula, an inner dielectric layer, a first coil, a second coil, a third coil, an outer dielectric layer, and an outer tube of the outer cannula. The inner tube defines a bore. The inner dielectric layer is secured onto an outer surface of the inner tube. The first, second, and third coils are wound over the inner dielectric layer. The outer dielectric layer is secured onto the first coil, the second coil, and the third coil. The outer tube is fastened to the outer dielectric layer.

20 Claims, 5 Drawing Sheets

(56) References Cited

U.S. PATENT DOCUMENTS

| | | |
|---|---|---|
| 6,235,038 B1 | 5/2001 | Hunter et al. |
| 6,253,770 B1 | 7/2001 | Acker et al. |
| 6,254,600 B1 | 7/2001 | Willink et al. |
| 6,336,906 B1 | 1/2002 | Hammarstrom et al. |
| 6,348,058 B1 | 2/2002 | Melkent et al. |
| 6,427,079 B1 | 7/2002 | Schneider et al. |
| 6,474,341 B1 | 11/2002 | Hunter et al. |
| 6,556,857 B1 | 4/2003 | Estes et al. |
| 6,610,066 B2 | 8/2003 | Dinger et al. |
| 6,615,155 B2 | 9/2003 | Gilboa |
| 6,616,651 B1 | 9/2003 | Stevens |
| 6,687,531 B1 | 2/2004 | Ferre et al. |
| 6,689,049 B1 | 2/2004 | Miyagi et al. |
| 6,695,764 B2 | 2/2004 | Silverman et al. |
| 6,747,539 B1 | 6/2004 | Martinelli |
| 6,796,988 B2 | 9/2004 | Melkent et al. |
| 6,833,814 B2 | 12/2004 | Gilboa et al. |
| 6,926,674 B2 | 8/2005 | Tenerz et al. |
| 6,940,941 B2 | 9/2005 | Gregerson et al. |
| 6,977,575 B2 | 12/2005 | Bernier |
| 6,980,849 B2 | 12/2005 | Sasso |
| 6,993,374 B2 | 1/2006 | Sasso |
| 7,001,045 B2 | 2/2006 | Gregerson et al. |
| 7,106,825 B2 | 9/2006 | Gregerson et al. |
| 7,108,421 B2 | 9/2006 | Gregerson et al. |
| 7,118,378 B1 | 10/2006 | Karapetyan |
| 7,188,998 B2 | 3/2007 | Gregerson et al. |
| 7,366,562 B2 | 4/2008 | Dukesherer et al. |
| 7,410,480 B2 | 8/2008 | Muni et al. |
| 7,462,175 B2 | 12/2008 | Chang et al. |
| 7,500,971 B2 | 3/2009 | Chang et al. |
| 7,537,594 B2 | 5/2009 | Sartor |
| 7,559,137 B2 | 7/2009 | Beer et al. |
| 7,604,609 B2 | 10/2009 | Jervis |
| 7,625,617 B1 | 12/2009 | Anderson et al. |
| 7,629,015 B2 | 12/2009 | Anderson et al. |
| 7,637,896 B2 | 12/2009 | Voegele et al. |
| 7,647,083 B2 | 1/2010 | Al-Ali et al. |
| 7,697,972 B2 | 4/2010 | Verard et al. |
| 7,751,865 B2 | 7/2010 | Jascob et al. |
| 7,763,035 B2 | 7/2010 | Melkent et al. |
| 7,774,933 B2 | 8/2010 | Wilson et al. |
| 7,797,032 B2 | 9/2010 | Martinelli et al. |
| 7,818,044 B2 | 10/2010 | Dukesherer et al. |
| 7,840,253 B2 | 11/2010 | Tremblay et al. |
| 7,844,319 B2 | 11/2010 | Susil et al. |
| 7,971,341 B2 | 7/2011 | Dukesherer et al. |
| 7,979,032 B2 | 7/2011 | Lomnitz |
| 8,075,969 B2 | 12/2011 | Anderson et al. |
| 8,086,298 B2 | 12/2011 | Whitmore, III et al. |
| 8,105,339 B2 | 1/2012 | Melkent et al. |
| 8,147,486 B2 | 4/2012 | Honour et al. |
| 8,239,001 B2 | 8/2012 | Verard et al. |
| 8,251,949 B2 | 8/2012 | Warnack |
| 8,255,027 B2 | 8/2012 | Al-Ali et al. |
| 8,504,139 B2 | 8/2013 | Jacobsen et al. |
| 8,648,605 B2 | 2/2014 | Nakamura et al. |
| 8,674,694 B2 | 3/2014 | Hyde et al. |
| 8,862,204 B2 | 10/2014 | Sobe et al. |
| 2001/0034549 A1 | 10/2001 | Bartholf et al. |
| 2002/0165448 A1 | 11/2002 | Ben-Haim et al. |
| 2003/0050552 A1 | 3/2003 | Vu |
| 2003/0187347 A1 | 10/2003 | Nevo et al. |
| 2004/0116803 A1 | 6/2004 | Jascob et al. |
| 2004/0199072 A1 | 10/2004 | Sprouse et al. |
| 2005/0027339 A1 | 2/2005 | Schrom et al. |
| 2005/0027340 A1 | 2/2005 | Schrom et al. |
| 2005/0027341 A1 | 2/2005 | Schrom et al. |
| 2005/0060885 A1 | 3/2005 | Johnson et al. |
| 2005/0085715 A1 | 4/2005 | Dukesherer et al. |
| 2005/0105212 A1 | 5/2005 | Sato |
| 2005/0137576 A1 | 6/2005 | Packard |
| 2005/0154294 A1 | 7/2005 | Uchiyama et al. |
| 2005/0171508 A1 | 8/2005 | Gilboa |
| 2005/0215922 A1* | 9/2005 | Tsonton et al. .............. 600/566 |
| 2005/0222554 A1 | 10/2005 | Wallace et al. |
| 2006/0025677 A1 | 2/2006 | Verard et al. |
| 2006/0036189 A1 | 2/2006 | Martinelli et al. |
| 2006/0084867 A1 | 4/2006 | Tremblay et al. |
| 2006/0129061 A1 | 6/2006 | Kaneto et al. |
| 2006/0206039 A1 | 9/2006 | Wilson et al. |
| 2006/0206170 A1 | 9/2006 | Denker et al. |
| 2006/0224142 A1 | 10/2006 | Wilson et al. |
| 2006/0235314 A1 | 10/2006 | Migliuolo et al. |
| 2007/0088416 A1 | 4/2007 | Atalar et al. |
| 2007/0157828 A1 | 7/2007 | Susel et al. |
| 2007/0197899 A1 | 8/2007 | Ritter et al. |
| 2007/0208252 A1 | 9/2007 | Makower |
| 2007/0220746 A1 | 9/2007 | Anderson et al. |
| 2008/0097195 A1 | 4/2008 | Urquhart et al. |
| 2008/0097347 A1 | 4/2008 | Arvanaghi |
| 2008/0119727 A1 | 5/2008 | Barbagli et al. |
| 2008/0119919 A1 | 5/2008 | Atalar et al. |
| 2008/0132909 A1 | 6/2008 | Jascob et al. |
| 2008/0171934 A1 | 7/2008 | Greenan et al. |
| 2008/0171937 A1 | 7/2008 | Dukesherer et al. |
| 2008/0172069 A1 | 7/2008 | Dukesherer et al. |
| 2009/0088728 A1 | 4/2009 | Dollar et al. |
| 2009/0118742 A1 | 5/2009 | Hartmann et al. |
| 2009/0171187 A1 | 7/2009 | Gerhart et al. |
| 2009/0204023 A1* | 8/2009 | Goldenberg ................ 600/567 |
| 2009/0209947 A1* | 8/2009 | Gordin et al. ................... 606/1 |
| 2010/0063383 A1* | 3/2010 | Anderson et al. ........... 600/411 |
| 2010/0081965 A1* | 4/2010 | Mugan et al. ............... 600/567 |
| 2010/0130852 A1 | 5/2010 | Neidert et al. |
| 2010/0185083 A1 | 7/2010 | Neidert et al. |
| 2010/0210939 A1* | 8/2010 | Hartmann et al. ........... 600/424 |
| 2010/0228117 A1 | 9/2010 | Hartmann |
| 2010/0234724 A1 | 9/2010 | Jacobsen et al. |
| 2010/0253361 A1 | 10/2010 | Nakamura et al. |
| 2010/0280363 A1 | 11/2010 | Skarda et al. |
| 2010/0331763 A1 | 12/2010 | Wilson et al. |
| 2011/0014705 A1 | 1/2011 | Leach et al. |
| 2011/0060214 A1 | 3/2011 | Makower |
| 2011/0066029 A1 | 3/2011 | Lyu et al. |
| 2011/0118592 A1 | 5/2011 | Sobe et al. |
| 2011/0251519 A1 | 10/2011 | Romoscanu |
| 2011/0258842 A1 | 10/2011 | Dukesherer et al. |
| 2011/0270081 A1 | 11/2011 | Burg et al. |
| 2012/0172696 A1 | 7/2012 | Kallback et al. |
| 2012/0197108 A1 | 8/2012 | Hartmann et al. |
| 2012/0197109 A1 | 8/2012 | Hartmann et al. |
| 2012/0197110 A1 | 8/2012 | Hartmann et al. |
| 2012/0245665 A1 | 9/2012 | Friedman et al. |
| 2012/0271135 A1 | 10/2012 | Burke et al. |
| 2012/0283570 A1 | 11/2012 | Tegg |
| 2013/0066194 A1 | 3/2013 | Seter et al. |
| 2013/0137954 A1 | 5/2013 | Jacobsen et al. |
| 2013/0317355 A1 | 11/2013 | Jacobsen et al. |
| 2014/0158555 A1 | 6/2014 | Nakamura et al. |
| 2014/0276004 A1 | 9/2014 | Strupeck et al. |
| 2015/0005625 A1 | 1/2015 | Sobe et al. |

FOREIGN PATENT DOCUMENTS

| | | |
|---|---|---|
| DE | 102009030731 A1 | 12/2010 |
| EP | 0425319 A2 | 5/1991 |
| EP | 1302172 A1 | 4/2003 |
| EP | 1552795 A1 | 7/2005 |
| EP | 1658818 A1 | 5/2006 |
| EP | 1743591 A2 | 1/2007 |
| EP | 1806756 A2 | 7/2007 |
| EP | 2123220 A1 | 11/2009 |
| EP | 2563260 A2 | 3/2013 |
| JP | 2000151041 A | 5/2000 |
| JP | 03-207344 B2 | 9/2001 |
| JP | 2006167119 A | 6/2006 |
| JP | 2007-527296 A | 9/2007 |
| JP | 2008-155033 A | 7/2008 |
| JP | 2008194475 A | 8/2008 |
| JP | 2010082446 A | 4/2010 |
| WO | WO-9632060 A1 | 10/1996 |
| WO | WO-9729682 A1 | 8/1997 |
| WO | WO-9729684 A1 | 8/1997 |

(56) References Cited

FOREIGN PATENT DOCUMENTS

| WO | WO-9940856 A1 | 8/1999 |
|---|---|---|
| WO | WO-0038571 A1 | 7/2000 |
| WO | WO-2006096685 A1 | 9/2006 |
| WO | WO-2006116597 A2 | 11/2006 |
| WO | WO-2008105874 A1 | 9/2008 |
| WO | WO-2009152486 A1 | 12/2009 |
| WO | WO-2010049834 A1 | 5/2010 |
| WO | WO-2010124285 A1 | 10/2010 |
| WO | WO-2010144419 A2 | 12/2010 |
| WO | WO-2011137301 A2 | 11/2011 |
| WO | WO-2012103304 A1 | 8/2012 |
| WO | WO-2012103407 A1 | 8/2012 |
| WO | WO-2012103410 A1 | 8/2012 |
| WO | WO-2013062869 A1 | 5/2013 |

OTHER PUBLICATIONS

"InstaTrak™ 3500 plus—Cranial. Multi-application electromagnetic surgical navigation system for ENT, Cranial, and Spine procedures." GE Healthcare http://www.gehealthcare.com/euen/surgery/products/instatrak-3500-plus-cranial/index.html (printed Dec. 14, 2009).

"InstaTrak™ 3500 plus—ENT. Multi-application electromagnetic surgical navigation system for ENT and Cranial." GE Healthcare http://www.gehealthcare.com/euen/surgery/products/instatrak-3500-plus-ent/index.html (printed Dec. 14, 2009).

"InstaTrak® Image Guided Sinus Surgery, Introduction to the InstaTrak System." Sinus-Clear.com http:/www.sinus-clear.com/instatrak.htm (printed Dec. 14, 2009).

"Mayfield® Skull Clamps and Headrest Systems," Mayfield® Surgical Devices Product Index, pp. 1-6, Dec. 2004 Integra LifeSciences Corporation.

"Medtronic O-Arm Multi-Dimensional Surgical Imaging System"; Brochure, 24pp, 2009.

"StealthStation_S7_System® Information Center in the OR," (2009) Medtronic, Inc.

"StealthStation® TRIA™ plus Treatment Guidance System," brochure, Medtronic Surgical Navigation Technologies (2004) 2 pages.

"The doctor can see you now" brochure. GE Medical Systems (2003) General Electric Company.

"TREON, StealthStation," brochure, Medtronic Surgical Navigation Technologies (2001) 8 pages.

Acclarent™ "Instructions for Use. Balloon Sinuplasty™ System. Relieva™ Devices, ReliENT™ Navigation System, and OptiLINK™ Extension." (Aug. 21, 2009) pp. 1-13.

Acclarent™ "Instructions for Use. Relieva Flex™ Sinus Guide Catheter, Relieva® Sinus Guide Catheter." (Sep. 19, 2009) pp. 1-6.

International Preliminary Report on Patentability mailed Nov. 15, 2012 for PCT/US2011/34475 claiming benefit of U.S. Appl. No. 13/097,243, filed Apr. 29, 2011.

International Search Report and Written Opinion mailed Feb. 6, 2013 for PCT/US2012/061086 claiming benefit of U.S. Appl. No. 13/281,001, filed Oct. 25, 2011.

International Search Report and Written Opinion mailed Jul. 6, 2012 for PCT/US2012/022840 claiming benefit to U.S. Appl. No. 13/016,762, filed Jan. 28, 2011.

International Search Report and Written Opinion mailed May 9, 2012 for PCT/US2012/022676 claiming benefit of U.S. Appl. No. 13/016,740, filed Jan. 28, 2011.

International Search Report and Written Opinion mailed May 9, 2012 for PCT/US2012/022846 claiming benefit of U.S. Appl. No. 13/016,765, filed Jan. 28, 2011.

International Search Report and Written Opinion mailed Oct. 31, 2011, claiming benefit of U.S. Appl. No. 13/097,243, filed Apr. 29, 2011.

Medtronic Navigation, "StealthStation® AXIEM™ Electromagnetic Navigation . . . ", 2005, www.stealthstation.com/physician/spine/library/axiem_ent.jsp, printed Aug. 19, 2006 (2 pages).

Examiner's Report dated Dec. 18, 2013 for Canadian Application No. 2,797,359 claiming benefit of U.S. Appl. No. 13/097,243, filed Apr. 29, 2011.

http://oxforddictionaries.com/definition/english/barrel (accessed Dec. 3, 2012).

International Preliminary Report on Patentability mailed Aug. 8, 2013 for PCT/US2012/022676 claiming benefit of U.S. Appl. No. 13/016,740, filed Jan. 28, 2011.

International Preliminary Report on Patentability mailed Aug. 8, 2013 for PCT/US2012/022840 claiming benefit of U.S. Appl. No. 13/016,762, filed Jan. 28, 2011.

International Preliminary Report on Patentability mailed Aug. 8, 2013 for PCT/US2012/022846 claiming benefit of U.S. Appl. No. 13/016,765, filed Jan. 28, 2011.

Japanese Office Action dated Jan. 7, 2014 for Japan Application No. 2013-508273 claiming benefit of U.S. Appl. No. 13/097,243, filed Apr. 29, 2011.

Chinese Office Action dated Sep. 3, 2014 for Chinese Application No. 201180031075.0 claiming benefit of PCT/US2011/034475 filed Apr. 29, 2011, claiming benefit from U.S. Appl. No. 61/330,024, filed Apr. 30, 2010 and U.S. Appl. No. 13/097,243, filed Apr. 29, 2011.

International Search Report and Written Opinion mailed Oct. 27, 2014 for PCT/US2014/028100 claiming benefit of U.S. Appl. No. 14/209,696, filed Mar. 13, 2014.

Invitation to Pay Additional Fees and Where Applicable, Protest Fee mailed Aug. 14, 2014 for PCT/US2014/028100 claiming benefit of U.S. Appl. No. 14/209,696, filed Mar. 13, 2014.

"Flexible electronics," Dec. 19, 2012 (Dec. 19, 2012), XP055112518, en.wikipedia.org. Retrieved form the Internet: <URL:http://en.wikipedia.orc/w/index.php?title=Flexible_electronics&oldid=528841651> [retrieved on Apr. 7, 2014]. (6 sheets).

"Flexible Printed Circuit Manufacturer—Capabilities," Aug. 16, 2012 (Aug. 16, 2012), XP055112534, fpcexpress.com. Retrieved from the Internet: URL: <http://web.archive.org/web/20120816030431/http://fpcexpress.com/capabilities.htm1>.

[retrieved on Apr. 7, 2014][retrieved on May 8, 2014]. (3 sheets).

"Minco Bulletin FC-3," Jul. 31, 2002 (Jul. 31, 2002). XP055115671, Retrieved from the Internet: <URL:http://www.temflexcontrols.com/pdf/fc3.pdf> [retrieved on Apr. 29, 2014]. (1 sheet).

"Sectional design standard for flexible printed boards," Internet Citation, Nov. 30, 1998 (Nov. 30, 1998), pp. 1-35, XP002691487, Retrieved form the Interent: <URL:http://222.184.16.210/smt/tzxt/bz/IPC-2223.pdf>. [retrieved on Feb. 1, 2013].

International Preliminary Report on Patentability and Written Opinion mailed May 8, 2014 for PCT/US2012/061086 claiming benefit of U.S. Appl. No. 13/281,001, filed Oct. 25, 2011.

International Search Report and Written Opinion mailed Apr. 23, 2014 for PCT/US2014/012786 claiming benefit of U.S. Appl. No. 13/748,150, filed Jan. 23, 2013.

International Search Report and Written Opinion mailed May 12, 2014 for PCT/US2014/012967 claiming benefit of U.S. Appl. No. 13/751,032, filed Jan. 25, 2013.

Japanese Office Action dated Aug. 29, 2016 for JP Application No. 2015-555345 corresponding to PCT/US2014/012967 which claims benefit of U.S. Appl. No. 13/751,032, filed Jan. 25, 2013.

Japanese Office Action dated Sep. 13, 2016 for JP Application No. 2016-510697 corresponding to PCT/US2014/034022 which claims benefit of U.S. Appl. No. 13/871,616, filed Apr. 26, 2013.

Communication pursuant to Article 94(3) EPC dated Nov. 24, 2016 for European Application No. 107084790 corresponding to PCT/US2010-026655 claiming benefit of U.S. Appl. No. 12/400,951, filed Mar. 10, 2009.

Communication pursuant to Article 94(3) EPC dated Feb. 1, 2017 for European Application No. 117199331 corresponding to PCT/US2011/034475 filed Apr. 29, 2011.

International Preliminary Report on Patentability and Written Opinion maile don Aug. 6, 2015 for PCT/US2014/012967 claiming benefit of U.S. Appl. No. 13/751,032, filed Jan. 25, 2013.

International Preliminary Report on Patentability and Written Opinion mailed on Aug. 6, 2015 for PCT/US2014/012786 claiming benefit of U.S. Appl. No. 13/748,150, filed Jan. 23, 2013.

(56) References Cited

OTHER PUBLICATIONS

Chinese Office Action dated Apr. 3, 2015 for Chinese Application No. 201180031075.0 claiming benefit of PCT/US2011/034475 filed Apr. 29, 2011, claiming benefit from U.S. Appl. No. 61/330,024, filed Apr. 30, 2010 and U.S. Appl. No. 13/097,243, filed Apr. 29, 2011.
Communication pursuant to Article 94(3) EPC for European Application No. 12703208.4-1654 dated Apr. 24, 2015.
International Preliminary Report on Patentability and Written Opinion mailed Sep. 24, 2015 for PCT/US2014/028100 claiming benefit to U.S. Appl. No. 14/209,696, filed Mar. 13, 2014.
International Preliminary Report on Patentability mailed Oct. 27, 2015 for PCT/US2014/034022 claiming benefit of U.S. Appl. No. 13/871,616, filed Apr. 26, 2013.
Chinese Office Action dated Feb. 4, 2017 for Chinese Application No. 2014800059516.
Chinese Office Action dated Mar. 9, 2017 for Chinese Application No. 201480004264.2.
European Office Action dated Mar. 1, 2017 for European Application No. 12709722.8.
Japanese Office Action dated May 19, 2017 for Japanese Application No. 2016-510697 corresponding to PCT/US2014/034022 which claims benefit of U.S. Appl. No. 13/871,616 filed Apr. 26, 2013.

\* cited by examiner

TRACKABLE BIOPSY NEEDLE

FIELD

The present disclosure relates to a trackable biopsy needle.

BACKGROUND

This section provides background information related to the present disclosure which is not necessarily prior art.

A biopsy is a medical test involving the removal of cells or tissues with a biopsy needle for examination. Due to the surgeon's viewing angle and/or surrounding tissue, it can be difficult for a surgeon to direct the biopsy needle to the area of interest. Surgical navigation systems can track the location of a biopsy needle handle or proximal region, which is opposite to a distal region including a needle tip, but if the tip moves or is moved relative to the handle and/or proximal region, then tracking the tip can become difficult.

SUMMARY

This section provides a general summary of the disclosure, and is not a comprehensive disclosure of its full scope or all of its features.

The present teachings provide for a trackable biopsy needle assembly including an inner tube of an outer cannula, an inner dielectric layer, a first coil, a second coil, a third coil, an outer dielectric layer, and an outer tube of the outer cannula. The inner tube defines a bore. The inner dielectric layer is secured onto an outer surface of the inner tube. The first, second, and third coils are wound over the inner dielectric layer. The outer dielectric layer is secured onto the first coil, the second coil, and the third coil. The outer tube is fastened to the outer dielectric layer.

The present teachings further provide for a trackable biopsy needle assembly including an outer cannula, a tip, and an inner cannula. The outer cannula includes an outer cannula hub, an outer tube extending from the outer cannula hub and defining a first outer layer, an inner tube affixed to the outer tube and defining a bore and a first inner diameter, and a plurality of conductive coils between the inner tube and the outer tube for tracking a position of the biopsy needle assembly within a magnetic field. The tip extends from a distal end of the outer cannula. The tip defines an outer biopsy window, a tip cavity aligned with the bore, a second outer diameter that is substantially the same as the first outer diameter, and a second inner diameter that is substantially the same as the first inner diameter. The inner cannula includes an inner cannula hub, an inner cannula shaft extending from the inner cannula hub, and an inner biopsy window defined by the inner cannula shaft proximate to an inner cannula shaft tip. The inner cannula shaft is sized to be received by the bore of the outer cannula and the tip cavity of the tip such that the inner biopsy window aligns with the outer biopsy window.

The present teachings also provide for a system for tracking a position of a trackable biopsy needle in a patient space. The system includes an outer cannula of the biopsy needle including a first coil, a second coil, and a third coil, each of which are between inner and outer tubes of the outer cannula and are angled relative to a longitudinal axis of the outer cannula; an electromagnetic tracking system including a localizer to generate an electromagnetic field for use in navigating the biopsy needle; an imaging system that images a patient to provide image data; and a navigation controller for receiving tracked information from the electromagnetic tracking system and the image data from the imaging system, where the navigation controller is configured to display the position of the biopsy needle on the image data.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

Figure 1:
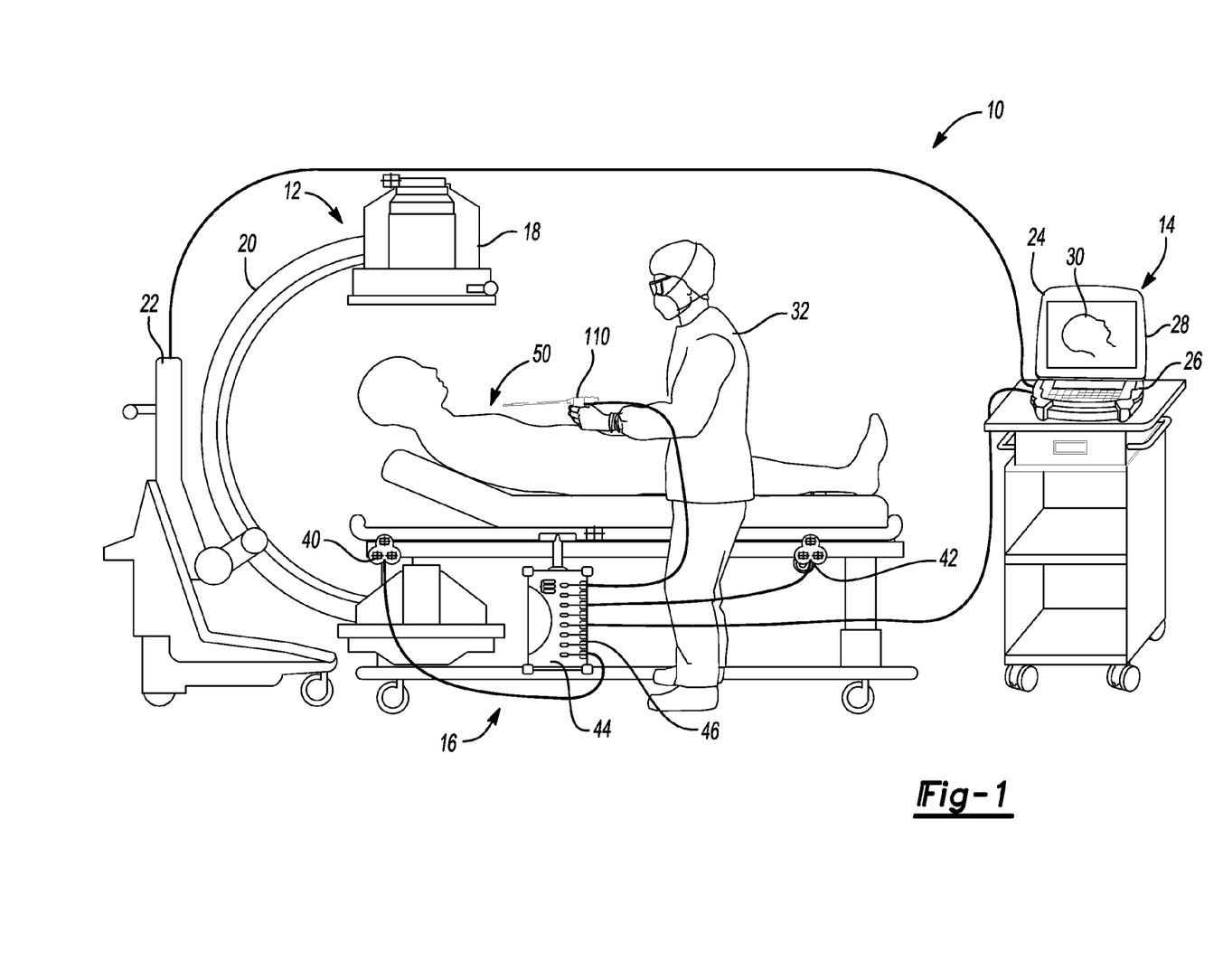
FIG. 1 is a perspective view of an exemplary navigation system according to the present teachings.

FIG. 1 is an overview of an image-guided navigation system 10 for use in the non-line-of-site navigating of an instrument, such as a biopsy needle assembly 110 according to the present teachings. Exemplary navigation systems include those disclosed in U.S. Pat. No. 7,366,562, issued Apr. 29, 2008, and U.S. Pat. App. Pub No. 2008/0132909, published Jun. 5, 2008, both of which are incorporated herein by reference. Commercial navigation systems include the StealthStation® AxiEM™ Surgical Navigation System by Medtronic Navigation, Inc. of Louisville, Colo., USA. It should be appreciated that while the navigation system 10 and biopsy needle assembly 110 are generally described in connection with a brain biopsy, the navigation system 10 and biopsy needle assembly 110 can be used in any other suitable procedure.

The navigation system 10 can identify and track the position of the biopsy needle assembly 110, including a distal end or tip thereof, as described further herein. The navigation system 10 generally includes an imaging system 12, a navigation controller 14, and an electromagnetic tracking system 16. The imaging system 12 includes a suitable imaging device, such as a digital or CCD camera 18 supported by a C-Arm mount 20 or an O-Arm mount, and an image device controller 22. Image data can be stored in the image device controller 22 and sent to the navigation controller 14. Description regarding the O-Arm imaging system or other appropriate imaging systems can be found in U.S. Pat. Nos. 7,188,998, 7,108,421, 7,106,825, 7,001,045 and 6,940,941, each of which is incorporated herein by reference.

The navigation controller 14 includes a computer 24 with a user interface 26 and a display 28 for displaying image data. The navigation controller 14 can also include or be connected to an image processor, navigation processor, and a memory to store instructions and data. The controller 14 can further include an optimization processor that assists with a navigated procedure. The image data need not be retained in the computer 24, but may also be directly transmitted to the navigation controller 14. Moreover, processing for the navigation controller 14 can all be done with single or multiple processors all of which may or may not be included in the navigation controller 14.

The navigation controller 14 provides facilities for displaying image data 30 as an image on the display 28, saving the image data 30, digitally manipulating the image data 30, or printing a hard copy of the image data 30. The user interface 26, which may be a keyboard, mouse, touch pen, touch screen or other suitable device, allows a physician or user 32 to provide inputs to control the imaging system 12, via the image device controller 22, or adjust the display settings of the display 28.

The EM tracking system 16 generally includes a localizer, such as a first localizing coil assembly or array 40 and/or a second localizing coil assembly or array 42, a coil array controller 44, a navigation probe interface 46, and the biopsy needle assembly 110. The biopsy needle assembly 110 can include an instrument tracking device or devices, such as electromagnetic coils, as will be discussed herein. The electromagnetic coils sense an electromagnetic field generated by the first and the second localizing coil arrays 40 and 42 and provide information to the navigation system 10 to determine a location of a needle tip or distal end of the needle assembly 110 to assist with navigation of the needle tip relative to a patient 50 within a surrounding patient space. The discussion of the EM tracking system 16 can be understood to relate to any appropriate tracking system. Exemplary electromagnetic systems are set forth in U.S. Pat. No. 5,913,820, entitled "Position Location System," issued Jun. 22, 1999 and U.S. Pat. No. 5,592,939, entitled "Method and System for Navigating a Catheter Probe," issued Jan. 14, 1997, each of which are hereby incorporated by reference.

Figure 2:
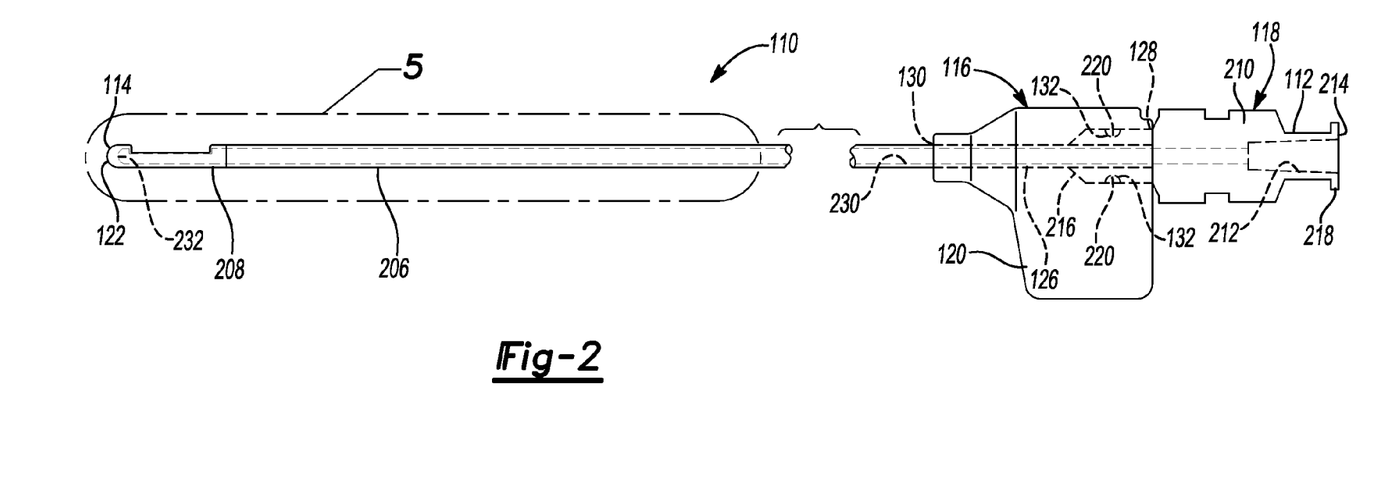
FIG. 2 is a plan view of a biopsy needle assembly according to the present teachings.

With reference to FIG. 2, the biopsy needle assembly 110 generally includes an overall proximal end 112, an overall distal end 114 that is opposite to the overall proximal end 112, an outer cannula 116, and an inner cannula 118.

The outer cannula 116 includes an outer cannula hub 120 near the overall proximal end 112, an outer cannula tip 122 at the overall distal end 114, and a sensor assembly 124 (FIGS. 3 and 3A), which extends between the outer cannula hub 120 and the outer cannula tip 122. The outer cannula hub 120 defines a hub through bore 126 including a first hub opening 128 and a second hub opening 130 at opposite ends of the hub through bore 126. The first hub opening 128 is closer to the overall proximal end 112 than the second hub opening 130 is and thus the first hub opening 128 is between the overall proximal end 112 and the second hub opening 130. The outer cannula hub 120 further defines one or more locking surfaces or tabs 132, which protrude into the hub though bore 126 and are configured to cooperate with the inner cannula 118 to secure the inner cannula 118 within the outer cannula 116, as further described herein.

With additional reference to FIGS. 3-6, the sensor assembly 124 generally includes an inner tube 134, an inner dielectric 136, a first coil 138, a second coil 140, a third coil 142, an outer dielectric 144, an adhesive 146, and an outer tube 148.

The inner tube 134 of the sensor assembly 124 includes an inner surface 150 (FIG. 4) and an outer surface 152 (FIG. 3), which is opposite to the inner surface 150. The inner surface 150 defines a sensor assembly bore 154 (FIG. 4) for receipt of the inner cannula 118, as further described herein. The inner tube 134 and the sensor assembly bore 154 extend from within the outer cannula hub 120 to the outer cannula tip 122. The inner tube 134 can be made of any suitable material, such as a polymeric material or a metal, such as stainless steel.

Figures 3, 3A:
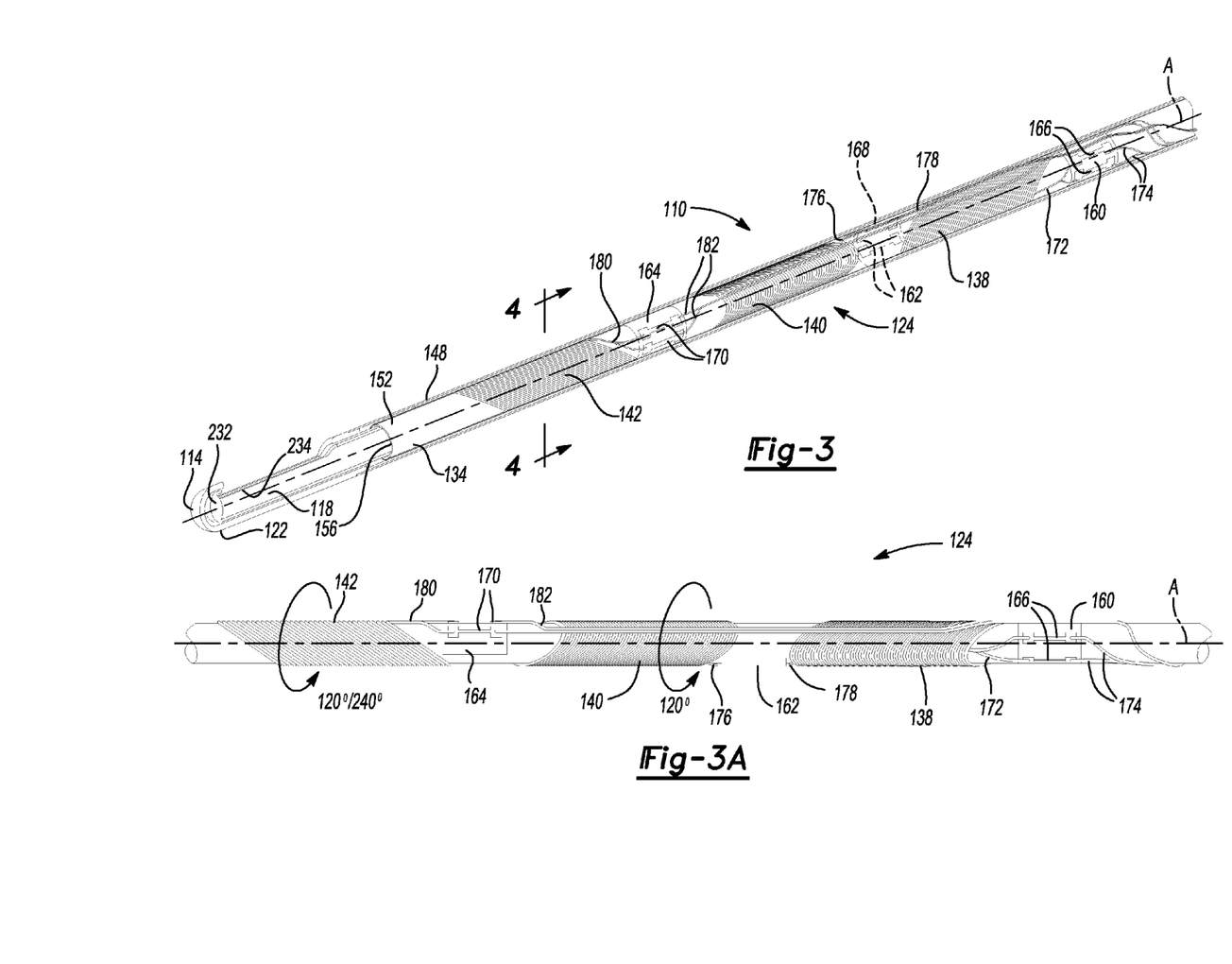
FIG. 3 is a perspective partial cross-sectional view of a distal area of the biopsy needle assembly of FIG. 2.
FIG. 3A is a side view of a sensor assembly of the biopsy needle assembly.
Figure 4:
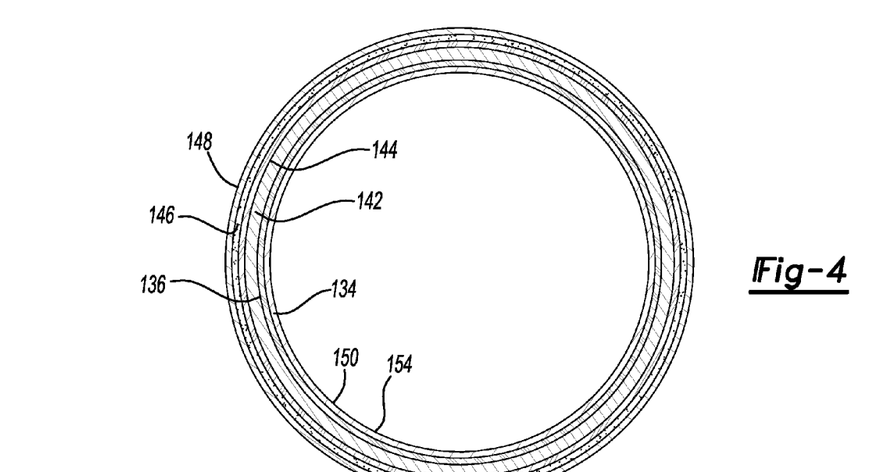
FIG. 4 is a cross-sectional view taken along line 4-4 of FIG. 3 with an inner cannula of the biopsy needle assembly removed for clarity.

The outer surface 152 of the inner tube 134 is covered with the inner dielectric 136. The inner dielectric 136 is a sleeve sized to fit over the inner tube 134. The inner dielectric 136 can be any suitable dielectric, such as a heat shrink tube. Any suitable heat shrink tube can be used, including part number 080100CST from Vention Medical of Salem, N.H., formerly Advanced Polymers. To secure the inner dielectric 136 to the outer surface 152, heat is applied to inner dielectric 136 to shrink the inner dielectric 136 onto the outer surface 152 of the inner tube 134.

The first, second, and third coils 138, 140, and 142 are wound onto the inner dielectric 136. The first coil 138 is closest (and more proximal) to the outer cannula hub 120, the third coil 142 is closest (or more distal) to the outer cannula tip 122, and the second coil 140 is between the first coil 138 and the third coil 142. Each of the first, second, and third coils 138, 140, and 142 are wound to provide two layers with 340 winds per layer. The first, second, and third coils 138, 140, and 142 are wound such that they each are angled or slanted at about 55° relative to a longitudinal axis A of the sensor assembly 124 (FIGS. 3 and 3A), the longitudinal axis A extending along an axial center of the sensor assembly bore 154. To hold each of the first, second, and third coils 138, 140, and 142 at the desired angle, a suitable adhesive can be used, such as Hollister Medical Adhesive 7730.

Each of the first, second, and third coils 138, 140, and 142 are clocked or rotated about the longitudinal axis A at about 120° relative to each other. For example and with reference to FIG. 3A, the second coil 140 is rotated about the longitudinal axis A about 120° relative to the first coil 138, and the third coil 142 is rotated about 120° relative to the second coil 140, or about 240° relative to the first coil 138. The first, second, and third coils 138, 140, and 142 are spaced about 13.5 millimeters apart as measured between center points of neighboring ones of the first, second, and third coils 138, 140, and 142 (see FIGS. 3 and 3A). The third coil 142 is spaced apart a suitable distance from a distal end 156 of the inner tube 134, such as about 5.0 millimeters from the most distal point of the third coil 142, or about 10.48 millimeters from a midpoint of the third coil 142. Any suitable conductive coil can be used, such as 58 AWG SP (single build polyurethane insulated) copper magnet wire conforming to NEMA MW79C. By arranging the first, second, and third coils 138, 140, and 142 as described above, the electromagnetic fields of the coils 138-142 are vectored at 90° relative to each other as described in U.S. Patent Publication No. 2010/0210939 (Ser. No. 12/770,181), filed on Apr. 29, 2010, which is incorporated herein by reference. Thus, six degrees of freedom information can be determined for the biopsy needle assembly 110 based on the positions of the first, second, and third coils 138, 140, and 142.

The sensor assembly further includes a first flexible printed circuit board or flex circuit 160, a second flexible printed circuit board or flex circuit 162, and a third flexible printed circuit board or flex circuit 164, each of which are mounted to the inner dielectric 136 with a suitable adhesive or any other suitable manner, such as disclosed in, for example, U.S. Patent Publication No. 2010/0234724 (Ser. No. 12/400,951), filed on Mar. 10, 2009, which is incorporated herein by reference. The first flex circuit 160 is mounted between the first coil 138 and the outer cannula hub 120. The second flex circuit 162 is mounted between the first coil 138 and the second coil 140. The third flex circuit 164 is mounted between the second coil 140 and the third coil 142. The first, second, and third flex circuits 160, 162, and 164 can be aligned with each other or rotated at various angles relative to each other, such as 120° relative to each other as illustrated in FIG. 3. Each of the first, second, and third flex circuits 160, 162, and 164 include a first pair of conductors 166, a second pair of conductors 168, and a third pair of conductors 170 respectively.

Ends of the first coil 138 are electrically connected to the first pair of conductors 166 of the first flex circuit 160 with a pair of first coil leads 172. Current is conducted between the first flex circuit 160 and the coil array controller 44 of the EM tracking system 16 with a pair of first cable leads 174, which extend between the first pair of conductors 166 and the coil array controller 44. Ends of the second coil 140 are electrically connected to the second pair of conductors 168 of the second flex circuit 162 with a pair of second coil leads 176. Current is conducted between the second flex circuit 162 and the coil array controller 44 of the EM tracking system 16 with a pair of second cable leads 178, which extend between the second pair of conductors 168 and the coil array controller 44. Ends of the third coil 142 are electrically connected to the third pair of conductors 170 of the third flex circuit 164 with a pair of third coil leads 180. Current is conducted between the third flex circuit 164 and the coil array controller 44 of the EM tracking system 16 with a pair of third cable leads 182, which extend between the third pair of conductors 170 and the coil array controller 44.

The first, second, and third coils 138, 140, and 142; the first, second, and third conductors 166, 168, and 170; and the associated leads are all covered with the outer dielectric 144. The outer dielectric 144 is positioned such that it covers and extends slightly beyond the third coil 142 toward the distal end 156, but terminates prior to the distal end of the inner tube 134. The outer dielectric 144 can be any suitable dielectric, such as a heat shrink tube. Any suitable heat shrink tube can be used, including part number 105100CST from Vention Medical of Salem, N.H., formerly Advanced Polymers. Heat is applied to the outer dielectric 144 to shrink it and secure the outer dielectric 144 in position.

Figure 5:
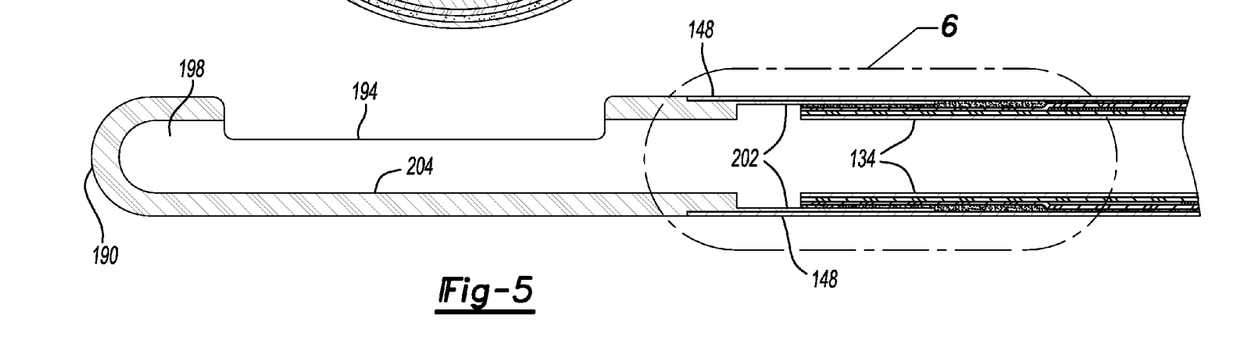
FIG. 5 is cross-sectional view of area 5 of FIG. 2 with the inner cannula of the biopsy needle assembly removed.
Figure 6:
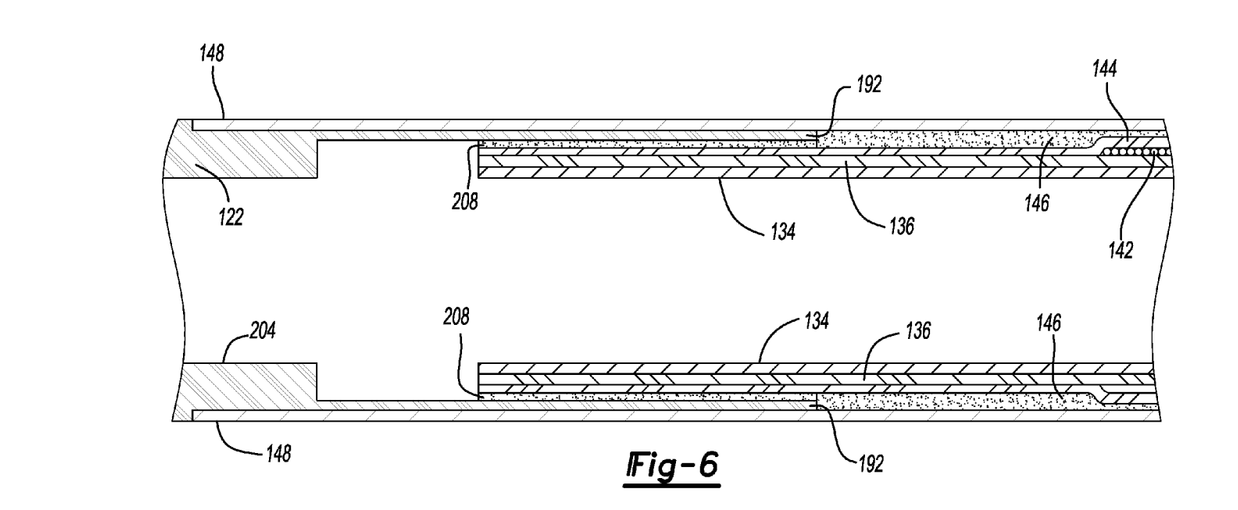
FIG. 6 is a cross-sectional view of area 6 of FIG. 5.

A suitable adhesive 146 (FIG. 4) is applied over the outer dielectric 144, except at an area between the distal end 156 of the inner tube 134 and the third coil 142. The inner tube 134 is inserted within the outer tube 148 to secure the outer dielectric 144 to the outer tube 148. Any suitable adhesive can be used, such as Loctite® adhesive number M-31CL by Henkel Corporation of Germany. The inner tube 134 is positioned such that the distal end 156 of the inner tube 134 does not extend beyond, but is rather recessed within the outer tube 148. Because the adhesive 146 is not included at the distal end 156 of the inner tube 134, a gap 186 is defined between the outer dielectric 144 and the outer tube 148 (FIGS. 5 and 6).

Figure 7:
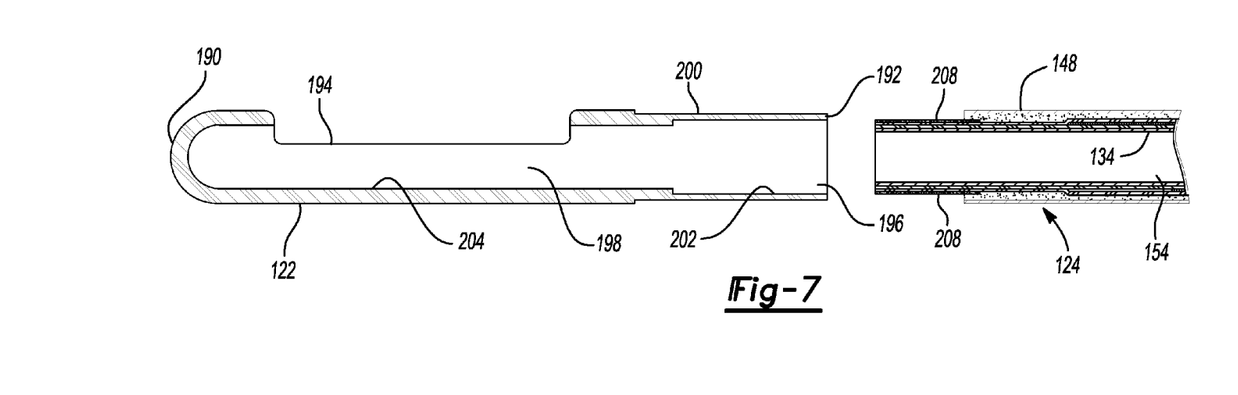
FIG. 7 is a cross-sectional view of a distal area of the biopsy needle assembly of FIG. 2 with an outer cannula tip removed from a remainder of the biopsy needle assembly.

With additional reference to FIG. 7 for example, the outer cannula tip 122 generally includes a rounded distal tip end 190 and a proximal tip end 192 opposite to the distal tip end 190. The outer cannula tip 122 defines an outer window 194 between the distal tip end 190 and the proximal tip end 192. The proximal tip end 192 defines a tip proximal opening 196, which provides access to a tip cavity 198 defined by the outer cannula tip 122. At the proximal tip end 192, the outer cannula tip 122 includes an outer recessed surface 200 and an inner recessed surface 202 that is opposite to the outer recessed surface 200.

The outer cannula tip 122 is positioned with respect to the sensor assembly 124 such that the proximal tip end 192 is seated within the gap 186 defined between the outer dielectric 144 and the outer tube 148. The outer tube 148 is thus over and generally surrounds the outer recessed surface 200, and the inner recessed surface 202 is over and generally surrounds outer surface 152 of the inner tube at the distal end 156 of the inner tube 134. An inner surface or diameter 204 of the outer cannula tip 122 distal to the inner recessed surface 202 is generally flush with the inner surface or diameter 150 of the inner tube 134 to provide a smooth surface for the inner cannula 118 to move along. Further, the outer tube 148 defines an outer diameter 206 that is generally flush with an outer diameter 208 of the outer cannula tip 122 (FIG. 2), to thereby provide the biopsy needle assembly 110 with a generally smooth overall outer surface between the cannula hub 120 and the overall distal end 114. Thus, the outer tube 148 and outer cannula tip 122 together provide a generally smooth inner surface or diameter 150/204 and a generally smooth outer surface or diameter 206/208 between the cannula hub 120 and the overall distal end 114. The inner cannula 118 can be any suitable inner cannula, and thus Applicants' outer cannula 116 with the sensor assembly 124 can be interchangeable with most any other inner cannula biopsy needle. By packaging the first, second, and third coils 138, 140, and 142 between the inner and outer tubes 134 and 148, the coils 138-142 are concealed and protected from damage.

The outer cannula tip 122 can be made of any suitable material, such as a suitable metallic or polymeric material, as illustrated. When the outer cannula tip 122 is made of a polymer, it may be over molded onto the sensor assembly 124. The outer cannula tip 122 can be secured to the sensor assembly 124 in any other suitable manner as well, such as with a suitable adhesive 208 or weld.

As illustrated in FIGS. 2 and 3, the inner cannula 118 includes an inner cannula hub 210, which defines a through bore 212 with a proximal opening 214 and a distal opening 216. At the proximal opening 214 is a flange 218 for cooperation with a syringe or other biopsy collection device. The flange 218 can be part of a Luer lock or any other suitable coupling device. Near the proximal opening 214, the through bore 212 is enlarged to accommodate the syringe or other biopsy collection device. At an exterior of the inner cannula hub 210 proximate to the distal opening 216 are locking recesses 220, which are configured to engage the locking surfaces 132 to retain the inner cannula 118 in cooperation with the outer cannula 116.

From the distal opening 216 of the inner cannula hub 210 extends elongated inner cannula shaft 230, which terminates at a shaft tip 232. The inner cannula shaft 230 has a length that is approximately equal to the combined length of the sensor assembly 124 and the outer cannula tip 122. Proximate to the shaft tip 232, is an inner cannula window 234 defined by the inner cannula shaft 230. When the outer window 194 is aligned with the inner cannula window 234, the biopsy sample of interest can be collected therethrough.

The biopsy sample is collected by rotating the inner cannula window 234, which is provided with a sharp edge, relative to the outer window 194.

Tracking the position of the biopsy needle assembly 110, particularly the overall distal end 114 thereof, will now be described. The EM tracking system 16 drives current through the first coil array 40 and optionally the second coil array 42 to generate an electromagnetic navigation field. The first, second, and third coils 138, 140, and 142 are each operable to sense the electromagnetic field and generate an output to the EM tracking system 16. Alternatively, the first, second, and third coils 138, 140, and 142 are each operable to generate the electromagnetic field that can then be received by the first and the second coil arrays 40 and 42.

Because every point in the navigation field is associated with a unique field strength, the electromagnetic tracking system 16 can determine the position of the instrument biopsy needle assembly 110 by measuring the field strength at each of the first, second, and third coils 138, 140, and 142. The coil array controller 44 can receive information regarding the field strength and transmit location information including x, y, and z position and roll, pitch, and yaw orientation information, of the tracked biopsy needle assembly 110. Accordingly, six degree of freedom information can be determined with the navigation system 10. Because the first, second, and third coils 138, 140, and 142 are arranged as described above, such as proximate to the overall distal end 114, the position of the overall distal end 114 can be more accurately determined.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A trackable biopsy needle assembly comprising:
    an inner tube of an outer cannula defining a bore and a first inner diameter configured to slidably receive an inner cannula therein, the inner tube including a first inner surface that is smooth along its length to slidably mate with a first outer surface of the inner cannula that is smooth along its length;
    an inner dielectric layer secured onto an outer surface of the inner tube;
    a first coil, a second coil, and a third coil wound over the inner dielectric layer;
    an outer dielectric layer secured onto the first coil, the second coil, and the third coil; and
    an outer tube of the outer cannula fastened to the outer dielectric, the outer tube defining a first outer diameter at a second outer surface thereof that is smooth along its length, the first coil, the second coil, and the third coil are between the inner tube of the outer cannula and the outer tube of the outer cannula;
    wherein the inner tube and the outer tube are fixed to one another and each one of the first coil, the second coil, and the third coil are adhesively embedded between the inner tube and the outer tube.

2. The biopsy needle assembly of claim 1, wherein the inner tube and the outer tube are formed of steel.

3. The biopsy needle assembly of claim 1, wherein the inner dielectric and the outer dielectric are each secured with a heat shrink; and
    wherein the outer tube of the outer cannula is fastened to the outer dielectric layer with an adhesive.

4. The biopsy needle assembly of claim 1, wherein each of the first coil, the second coil, and the third coil are wound into a first layer and a second layer.

5. The biopsy needle assembly of claim 4, wherein each first layer and each second layer include 340 coil winds.

6. The biopsy needle assembly of claim 1, wherein the first coil, the second coil, and the third coil are each wound at an angle of 55° relative to a longitudinal axis of the outer cannula.

7. The biopsy needle assembly of claim 6, wherein the first coil, the second coil, and the third coil are each rotated at 120° relative to one another about the longitudinal axis.

8. The biopsy needle assembly of claim 1, wherein the first coil, the second coil, and the third coil are spaced 13.5 millimeters apart as measured between center points of each of the first coil, the second coil, and the third coil.

9. The biopsy needle assembly of claim 1, wherein the third coil is spaced apart 5.0 millimeters from a distal end of the inner tube.

10. The biopsy needle assembly of claim 1, further comprising a tip defining an outer biopsy window, the tip fastened to a distal end of at least one of the inner tube and the outer tube, the tip defining a second inner diameter that is the same as the first inner diameter and a second outer diameter that is the same as the first outer diameter.

11. The biopsy needle assembly of claim 1, further comprising a tip defining an outer biopsy window, a second inner diameter that is the same as the first inner diameter, and a second outer diameter that is the same as the first outer diameter;
    wherein a proximal end of the tip is secured between the outer tube and the inner tube.

12. The biopsy needle assembly of claim 11, wherein the tip is secured with an over mold.

13. The biopsy needle assembly of claim 1, further comprising:
    a first flexible circuit between the first coil and a proximal end of the inner tube, the first coil is connected to the first flexible circuit with a first coil lead, the first circuit is configured to be connected to a coil array controller of an electromagnetic tracking system with a first cable lead;
    a second flexible circuit between the first coil and the second coil, the second coil is connected to the second flexible circuit with a second coil lead, the second circuit is configured to be connected to the coil array controller with a second cable lead; and
    a third flexible circuit between the second coil and the third coil, the third coil is connected to the third flexible circuit with a third coil lead, the third circuit is configured to be connected to the coil array controller with a third cable lead.

14. The biopsy needle assembly of claim 10, further comprising the inner cannula defining an inner biopsy window and configured to be received within the bore defined by the inner tube such that the inner biopsy window is aligned with the outer biopsy needle.

15. A trackable biopsy needle assembly comprising:
    an outer cannula including:
        an outer cannula hub;

an outer tube extending from the outer cannula hub and defining a first outer diameter, the outer tube is smooth along its entire length at the first outer diameter;

an inner tube affixed to the outer tube, the inner tube defining a bore and a first inner diameter, the inner tube is smooth along its entire length at the first inner diameter; and a plurality of conductive coils between the inner tube and the outer tube for tracking a position of the biopsy needle assembly within a magnetic field;

a tip extending from a distal end of the outer cannula, the tip defining an outer biopsy window, a tip cavity aligned with the bore, a second outer diameter that is the same as the first outer diameter, and a second inner diameter that is the same as the first inner diameter; and an inner cannula including:
an inner cannula hub;
an inner cannula shaft extending from the inner cannula hub, the inner cannula defining a third outer diameter, the inner cannula shaft is smooth along its entire length at the third outer diameter and configured to slidably mate with the inner tube at the first inner diameter thereof; and
an inner biopsy window defined by the inner cannula shaft proximate to an inner cannula shaft tip;
wherein the inner cannula shaft is sized to be received by the bore of the outer cannula and the tip cavity of the tip such that the inner biopsy window aligns with the outer biopsy window, the inner cannula is movable relative to the outer cannula.

16. The biopsy needle assembly of claim 15, wherein the plurality of conductive coils include a first coil, a second coil, and a third coil each connected to a first flexible circuit, a second flexible circuit, and a third flexible circuit respectively; and
wherein each of the first coil, the second coil, and the third coil are wound into a first layer including 340 coil winds and a second layer including 340 coil winds.

17. The biopsy needle assembly of claim 16, wherein the first coil, the second coil, and the third coil are each wound at 55° relative to a longitudinal axis of the outer cannula;
wherein the third coil is spaced apart 5.0 millimeters from a distal end of the inner tube; and
wherein the first coil, the second coil, and the third coil are spaced 13.5 millimeters apart as measured between center points of each of the first coil, the second coil, and the third coil.

18. A system for tracking a position of a trackable biopsy needle in a patient space comprising:
an outer cannula of the biopsy needle including a first coil, a second coil, and a third coil, each of which are adhesively embedded between fixed inner and outer tubes of the outer cannula and angled relative to a longitudinal axis of the outer cannula, the inner tube has a smooth inner surface along its entire length defining a constant inner diameter that defines a bore therethrough, the outer tube has a smooth outer surface along its entire length defining a constant first outer diameter;
an inner cannula configured to be slidably received within the inner tube of the outer cannula, the inner cannula has a second smooth outer surface along its entire length defining a constant second outer diameter, the second smooth outer surface configured to slidably mate with the smooth inner surface of the inner tube;
a first flexible circuit between the first coil and a proximal end of the inner tube, the first coil is connected to the first flexible circuit with a first coil lead, the first circuit is configured to be connected to a coil array controller of an electromagnetic tracking system with a first cable lead;
a second flexible circuit between the first coil and the second coil, the second coil is connected to the second flexible circuit with a second coil lead, the second circuit is configured to be connected to the coil array controller with a second cable lead;
a third flexible circuit between the second coil and the third coil, the third coil is connected to the third flexible circuit with a third coil lead, the third circuit is configured to be connected to the coil array controller with a third cable lead;
the electromagnetic tracking system including a localizer to generate an electromagnetic field for use in navigating the biopsy needle;
an imaging system that images a patient to provide image data; and
a navigation controller for receiving tracking information from the electromagnetic tracking system and the image data from the imaging system, where the navigation controller is configured to identify the position of the biopsy needle on the image data.

19. The system of claim 18, wherein the first coil, the second coil, and the third coil are connected to the localizer with individual cable leads.

20. The system of claim 18, wherein the first coil, the second coil, and the third coil are each wound into a first layer including 340 coil winds and a second layer including 340 coil winds;
wherein the first coil, the second coil, and the third coil are each wound at 55° relative to the longitudinal axis of the outer cannula;
wherein the first coil, the second coil, and the third coil are each rotated at 120° relative to each other about the longitudinal axis; and
wherein the third coil is spaced apart about 5.0 millimeters from a distal end of the outer cannula.

* * * * *